(12) United States Patent
Xie et al.

(10) Patent No.: US 7,908,930 B2
(45) Date of Patent: Mar. 22, 2011

(54) SYSTEMS AND METHODS FOR MEASURING MULTIPHASE FLOW IN A HYDROCARBON TRANSPORTING PIPELINE

(75) Inventors: Cheng-Gang Xie, Sawston (GB); Yan Kuhn de Chizelle, Houston, TX (US); Jacques Jundt, Newton, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 290 days.

(21) Appl. No.: 12/067,757

(22) PCT Filed: Aug. 15, 2006

(86) PCT No.: PCT/GB2006/003039
§ 371 (c)(1),
(2), (4) Date: Sep. 2, 2008

(87) PCT Pub. No.: WO2007/034132
PCT Pub. Date: Mar. 29, 2007

(65) Prior Publication Data
US 2008/0319685 A1     Dec. 25, 2008

(30) Foreign Application Priority Data
Sep. 23, 2005 (GB) .................................. 0519374.3

(51) Int. Cl.
*G01F 1/74* (2006.01)
(52) U.S. Cl. .................................................. 73/861.04
(58) Field of Classification Search ............... 73/861.04; 702/50
See application file for complete search history.

(56) References Cited

U.S. PATENT DOCUMENTS

| 4,289,020 A | 9/1981 | Paap |
| 4,996,490 A | 2/1991 | Scott et al. |
| 5,014,010 A | 5/1991 | Helms et al. |

(Continued)

FOREIGN PATENT DOCUMENTS
EP  0032061 A1  7/1981

(Continued)

OTHER PUBLICATIONS

Atkinson et al, New generation multiphase flowmeters from Schlumberger and Framo Engineering AS:, 17th North Sea Flow Measurement Workshop, Oslo, Norway, Oct. 25-28, 1999, pp. 154-165.

(Continued)

*Primary Examiner* — Jewel Thompson
(74) *Attorney, Agent, or Firm* — Vincent Loccisano; James McAleenan; Brigid Laffey

(57) ABSTRACT

This disclosure relates in general to methods and systems for measuring multiphase flows in a pipeline using a combination of venturi, microwave and radiation techniques, where the pipeline is configured to transport hydrocarbons. More specifically, but not by way of limitation, certain embodiments of the present invention provide methods and systems in which low activity radiation sources may be used in combination with one or more microwave transmitter-receiver pairs and pressure differential sensors to measure the flow rates and fractions of phases in multiphase flows in a pipeline, such as may be encountered in producing hydrocarbon wells. Additionally, other embodiments of the present invention provide for the arrangement of one or more microwave transmitter-receiver pairs, one or more radiation source-detector pairs and/or one or more pressure sensor ports in the same cross-section of the throat of a venturi to measure multiphase flow in a hydrocarbon transporting pipeline.

45 Claims, 4 Drawing Sheets

U.S. PATENT DOCUMENTS

| | | | |
|---|---|---|---|
| 5,025,222 A | 6/1991 | Scott et al. | |
| 5,101,163 A | 3/1992 | Agar | |
| 5,107,219 A | 4/1992 | Marrelli et al. | |
| 5,157,339 A | 10/1992 | Scott et al. | |
| 5,243,290 A | 9/1993 | Safinya et al. | |
| 5,259,239 A | 11/1993 | Gaisford | |
| 5,272,444 A | 12/1993 | Cox | |
| 5,412,326 A | 5/1995 | Marrelli et al. | |
| 5,485,743 A | 1/1996 | Taherian et al. | |
| 5,503,004 A | 4/1996 | Agar | |
| 5,551,305 A | 9/1996 | Farchi et al. | |
| 5,597,961 A | 1/1997 | Marrelli | |
| 5,625,293 A | 4/1997 | Marrelli et al. | |
| 5,644,244 A | 7/1997 | Marrelli et al. | |
| 5,741,977 A | 4/1998 | Agar et al. | |
| 5,748,002 A | 5/1998 | Scott et al. | |
| 5,793,216 A | 8/1998 | Constant | |
| 5,966,017 A | 10/1999 | Scott et al. | |
| 6,332,111 B1 * | 12/2001 | Fincke | 702/50 |
| 6,935,189 B2 * | 8/2005 | Richards | 73/861.04 |
| 2004/0182172 A1 * | 9/2004 | Richards | 73/861.04 |
| 2005/0188771 A1 | 9/2005 | Lund Bo et al. | |

FOREIGN PATENT DOCUMENTS

| | | |
|---|---|---|
| EP | 0236623 A1 | 9/1987 |
| GB | 2359435 A | 8/2001 |
| WO | 9321501 A1 | 10/1993 |
| WO | 9910712 A1 | 3/1999 |
| WO | 9923469 A1 | 5/1999 |
| WO | 9963331 A3 | 12/1999 |
| WO | 0125762 A1 | 4/2001 |
| WO | 0161283 A1 | 8/2001 |
| WO | 03034051 A1 | 4/2003 |
| WO | 2005057142 A1 | 6/2005 |

OTHER PUBLICATIONS

Butler, "Results of field testing of high gas void fraction meters in Canada, United States, Venezuela, the Middle East and Sumatra", 1997 Multiphase Metering Conference, IBC Technical Services, Aberdeen, Scotland, Mar. 12-13, 1997.

Hammer, "Flow permittivity models and their application in multiphase meters", Proc. Multiphase Metering, IBC Technical Services, Aberdeen, Scotland, Mar. 12-13, 1997.

Hewitt, "Differential pressure, dual energy gamma densitometry and cross correlation in multiphase flow measurement", International Conference on the Future of Multiphase Metering, London, England, Mar. 26-27, 1998.

Kalsaas et al, "Operational experience with multiphase meters at Vigdis", 17th North Sea Flow Measurement Workshop, Oslo, Norway Oct. 25-28, 1999, pp. 362-375.

Lund Bo et al, "Application of microwave spectroscopy for the detection of water fraction and water salinity in water/oil/gas pipe flow", Journal of Non-Crystalline Solids, vol. 305, 2002, pp. 345-353, XP-004358872.

Marrelli, "Starcut multiphase meter - smart measurements of watercut in multiphase fluids using compact partial separation methods", International Conference on the Future of Multiphase Metering, London, England, Mar. 26-27, 1998.

Myrvang Gulbraar et al, "Compact cyclone multiphase meter (CCM) discussion of metering principle, slug handling capacities and flow measurement results", 17th North Sea Flow Measurement Workshop, Oslo, Norway, Oct. 25-28, 1999, pp. 178-192.

Stogryn, "Equations for calculating the dielectric constant of saline water", IEEE Transaction son Microwave Theory and Techniques, vol. 19, 1971, pp. 733-736.

Wee, "Multiphase measurement system with fully redundant measurements to improve accuracy and simplify maintenance", 17th North Sea Flow Measurement Workshop, Oslo, Norway, Oct. 25-28, 1999, pp. 346-361.

* cited by examiner

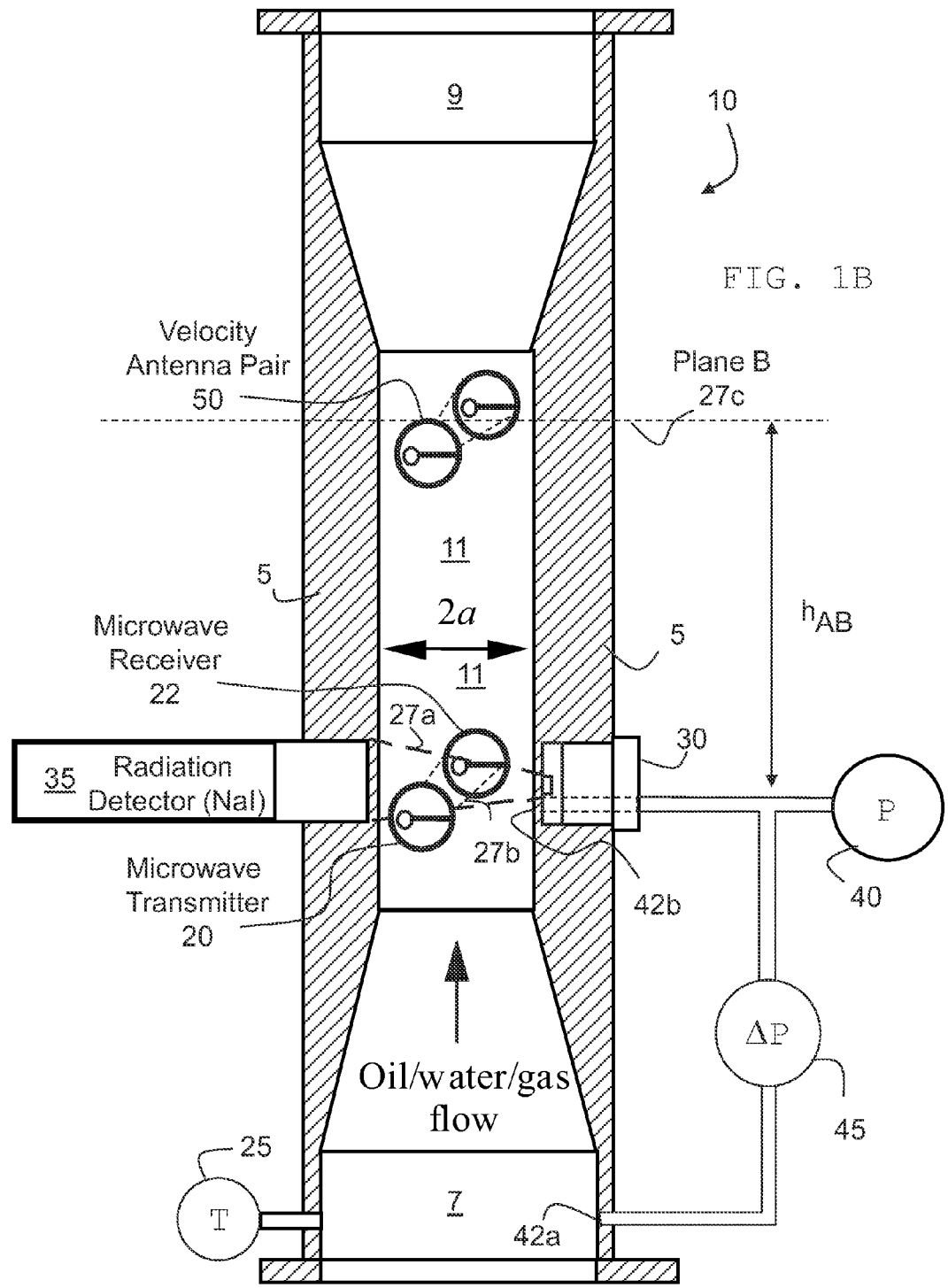

though the pipeline. The problems associated with taking measurements arise, from among other things, the distribution of the three phases in the pipe—the phases may form different arrangements temporally and spatially—both axially and radially in the pipe. These different arrangements of the multiple phases may create, among other things, nonlinear responses—with the measuring system.

SYSTEMS AND METHODS FOR MEASURING MULTIPHASE FLOW IN A HYDROCARBON TRANSPORTING PIPELINE

CROSS-REFERENCE TO RELATED APPLICATIONS

This application claims the benefits of priority under 35 U.S.C. §119 to:
i) Application Number 0519374.3, entitled "SYSTEMS AND METHODS FOR MEASURING MULTIPHASE FLOW IN A HYDROCARBON TRANSPORTING PIPELINE," filed in the United Kingdom on Sep. 23, 2005; and
ii) Application Number PCT/GB2006/003039, entitled "SYSTEMS AND METHODS FOR MEASURING MULTIPHASE FLOW IN A HYDROCARBON TRANSPORTING PIPELINE" filed under the PCT on Aug. 15, 2006;
which are incorporated herein by reference in their entirety for all purposes.

BACKGROUND OF THE INVENTION

This disclosure relates in general to methods and systems for measuring multiphase flows in a pipeline using a combination of venturi, microwave and radiation techniques, where the pipeline is configured to transport hydrocarbons. More specifically, but not by way of limitation, certain embodiments of the present invention provide methods and systems in which low activity radiation sources may be used in combination with one or more microwave transmitter-receiver pairs and a pressure differential sensor to measure the flow—fractions and rates of phases—in multiphase flows in a pipeline, such as may be encountered in producing hydrocarbon wells. Additionally, other embodiments of the present invention provide for the arrangement of one or more microwave transmitter-receiver pairs, one or more radiation source-detector pairs and/or one or more pressure sensor ports in the same cross-section of the throat of a venturi to measure multiphase flow in a hydrocarbon transporting pipeline.

It is desirable during the production of oil and gas to carry out flow measurements to determine the flow in a hydrocarbon transporting pipeline of individual phases of multiphase flow where the multiphase flow may consist of a two-phase or a three-phase combination of oil/water/gas. Measurements may be made in the form of mass flow rate or volume flow rate of a so-called multiphase measurement. Preferably, flow measurements may be performed using temporarily or permanently installed compact flow measurement systems that—unlike many conventional separator-based measurement systems, which separate multiphase flow into its components and then measure the flow of the component phases—are capable of measuring the flow of the phases of the multiphase flow without separation.

Measurement of the flow of the different phases—i.e. oil, gas and water—in an oil/hydrocarbon transporting pipeline is often highly desirable so as to control and regulate hydrocarbon production. For example, it may be important to measure oil being produced by not only an oilfield, but also individual oil wells associated with the oilfield. Measurements may be necessary/desirable in order to determine the water and/or the gas content of the flow being produced from individual oil wells—for production analysis, etc—and/or to allocate production amounts to individual rights owners. It is, however, in general, very difficult to obtain measurements of the flow of the different phases when the different phases—oil, water and gas—flow simultaneously through the pipeline. The problems associated with taking measurements arise, from among other things, the distribution of the three phases in the pipe—the phases may form different arrangements temporally and spatially—both axially and radially in the pipe. These different arrangements of the multiple phases may create, among other things, nonlinear responses—with the measuring system.

Flow of the multiphase fluid in the pipe may consist, among other flow designations, of a continuous phase—normally, liquid flow—or a discontinuous phase—normally, gas flow. In the continuous phase, the flow may be a continuous oil flow and the flowing oil may contain water droplets. Such flow, being primarily made up of a hydrocarbon substance, may, in general, be marked by low conductance characteristics. In the alternative, the flow may be a continuous water flow with oil droplets distributed in the continuously flowing water. In such situations, the water, which may also have varying degrees of salinity, may provide that the flowing mixture has electrically conductive characteristics that change with time due to water injection or breakthrough, especially in contrast to the oil continuous situation.

With regard to the gas in the multiphase fluid, the gas may be distributed in large volumes or pockets in the multiphase fluid as gas chums or slugs, or may be distributed as small bubbles in the liquid phase, often referred to as bubble flow. Furthermore, under high pressure, such as down-hole, gas in the multiphase fluid may be dissolved in the oil phase. When there are large volumes of gas in the pipeline the gas may govern the multiphase fluid flow and cause the oil and water phase to be pushed back to the pipe wall. In this case, often referred to as annular flow, the oil/water fluid mixture may move at a low velocity along the pipe wall. Additionally annular-mist flow may occur when gas flow dominates the multiphase flow in the pipe (and in mist flow, neither the water phase nor the oil phase is continuous). In such annular-mist flow, gas-carrying droplets of oil or water may move up the center of the pipe at high velocity while the remaining oil or water flows up along the pipe walls at low velocity.

In general, the liquid—which may be formed from multiple liquid phases mixed together—moves with a common velocity through the pipeline. However, in low flow velocity situations the oil and water may become partially or even completely separated. In such situations, the water and oil may travel at different velocities through the pipeline. For a non-horizontal pipe, the lighter oil may move up the pipe faster than the heavier water and cause small water drops to form that may in turn aggregate to form larger drops or slugs that may reach pipe diameter. This type of flow is often referred to as slug flow. The difference in velocity of the oil and water moving through the pipe is often referred to as "slip". Because gas has a substantially lower density than oil/water or a mixture of the two, a larger slip will occur between the gas and the liquid phases.

To measure accurately the flow of the different phases of oilfield oil-water-gas multiphase flows, it is desirable to have a multiphase flow meter ("MPFM") capable of robust flow rate measurement for all the different flow regimes—including both water-continuous flows (high water cut) and oil-continuous flows—and over a wide range of water salinity and oil viscosity. For topside applications, however, it may be difficult to obtain high-accuracy flow rate measurements because of flow instabilities, including those discussed in more detail above, such as slug, chum, annular flow, etc. Furthermore, due to these instabilities, it is often very difficult to measure water-cut using an in-line MPFM, especially for high gas-cuts. As such there exists in the art a long felt need in the art for a versatile MPFM that is capable of accurately measuring multiphase flow over a wide range of conditions. While several different MPFMs have been designed to measure multiphase flow and/or phase content of the multiphase flow, as discussed below, these designs have many design drawbacks, such as requiring the use of high-activity/non-exempt radiation sources and the requirement of interpolation of measurements because of the configuration of the different measuring apparatus in the MPFM.

U.S. Pat. No. 4,289,020 ("the '020 patent) describes a system for the limited purpose of measuring water-cut in a multiphase fluid when gas is present. As such, the '020 patent does not disclose or teach measuring actual multiphase flow in a pipe and, consequently, it does not disclose how to address the issues associated with such measurements. The '020 patent discloses using a combined transmission-microwave and gamma-ray density measuring system to measure the water-cut in the multiphase fluid with gas present. In the system, the microwave and gamma ray beams are configured obliquely with respect to the flow axis of the multiphase fluid through the pipe that is being measured. Water-cut is calculated directly from the amplitude attenuation of the microwaves passing through the multiphase fluid and the transmission of gamma rays through the multiphase fluid.

The method disclosed in the '020 patent has many limitations including but not limited to: the method is not robust—there is no solid physical basis for determining oil/water fraction purely from microwave attenuation; determining water cut based on amplitude attenuation may be inaccurate due to nonlinear attenuation effect; and the method does not provide for the use of low activity radiation sources. Embodiments of the current invention differ substantially from the '020 patent. Embodiments of the current invention provide robust measurement of phase flow that avoids nonlinearity inaccuracies by basing fluid phase measurements on permittivity and conductivity of the multiphase fluid. Embodiments of the current invention utilize pressure differential measurements provide for the use of low activity radiation sources. Embodiments of the present invention also provide for the microwave transmitter-receiver pair to be aligned in the same cross-section (as that the low-activity radiation source-detector pair is aligned), rather than oblique to the multiphase flow, to reduce the distance traversed by the microwave beam and the resultant phase wrapping effect, which may provide for using the MPFMs in larger diameter pipes and in high salinity conditions.

U.S. Pat. No. 5,101,163 ("the '163 patent) discloses measuring water fraction in an oil/water mixture by using at least one transmitting antenna and two receiving antennas. As disclosed, antennas are designed to emit and receive operating frequencies around 2.45 GHz through the multiphase fluid. The phase difference and/or the power ratio of the two received signals are determined and used with a look-up table to yield water fraction. The '163 patent discloses installing the antennas axially in such a way that one receiving antenna receives signal in the flow direction, while the other equally-spaced antenna receives its signal against the flow direction to provide for measurement of the phase difference of signals received by the two antennas, which is directly related to the flow velocity. The '163 patent does not disclose how to make corrections for instabilities in the flow due to gas nor does it disclosed how the microwave receivers' amplitude/phase difference or ratio measurements at 2.45 GHz compensate for changes in water salinity—different water salinities will cause the multiphase fluid containing the water to interact differently with the microwaves and to cause different amplitude attenuations and phase shifts.

Unlike the present invention, the '163 patent provides a method/system for measuring multiphase fluid flow that is entirely empirical and lacks a solid physics basis. Further, the '163 patent does not disclose using radiation density measurements in connection with the microwaves to make measurements that take account of multiphase fluid flow inconsistencies, including but not limited to flow inconsistencies caused by gas.

U.S. Pat. No. 5,259,239 ("the '239 patent) discloses a hydrocarbon mass flow meter that uses the principle that the permittivity of a dry hydrocarbon—oil and/or gas—is closely related to its density. As such, by determining the mixture density using a gamma-ray densitometer, the changes in the hydrocarbon permittivity can be compensated for and the flow of the phases of the multiphase fluid determined. Unlike embodiments of the current invention, the '239 patent does not disclose oil/water mixture permittivity and conductivity corrections for salinity, use of pressure change monitoring to provide for the use of a low-activity radiation source nor does it disclose configuring the microwave measuring device and the radiation densitometer in the same cross-section to eliminate interpretation factors for axially developing phase-fractions and velocities in the multiphase flow measurement.

SUMMARY OF THE INVENTION

This disclosure relates in general to methods and systems for measuring multiphase flows in a pipeline using a combination of microwave and radiation techniques, preferably a combination of venturi, microwave and radiation techniques, where the pipeline is configured to transport hydrocarbons.

In a preferred embodiment of the present invention a low activity radiation source is used to determine an average density of the multiphase mixture passing through a perpendicular cross-section of the full-width pipeline or the throat section of the venturi, measuring a parameter that changes in relation to density changes in the multiphase mixture as it passes through the pipeline or the venturi, using measurements of the parameter to convert the average density to a "fast" density, measuring permittivity and/or conductivity of the multiphase mixture in the venturi and processing the multiphase flow of the multiphase mixture in the venturi from the fast density and one or a combination of the permittivity and conductivity. As the properties of the flow can vary rapidly in direction of the flow along the length of the pipe, the microwave measurement and the radiation density measurements in this preferred embodiment are taken over the same perpendicular cross-section of the pipe or throat. Microwave antennae and radiation source window and detector window to the flow are thus located at essentially at the same circumference of the pipe.

A flow velocity may preferably be measured using a pressure drop measurement in the venturi or, alternatively or additionally, through other velocity measurements such as cross-correlation with at second microwave antennae system.

In another embodiment, cross-sectional flow of different phases in a multiphase mixture in a pipeline at a particular location may be determined from measurements of conductivity and/or permittivity of the multiphase mixture located in the throat of a venturi, determined from a microwave transmitter-receiver pair, and mixture density of the multiphase mixture in the throat of the venturi, measured from readings from a radiation source and detector, wherein the microwave transmitter-receiver pair and the radiation source and detector are all located on a single cross-section of the throat of the venturi.

In certain aspects, a differential pressure sensor for measuring differential pressure in the venturi includes a pressure port located on the cross-section. Further, in many aspects the venturi is vertical and the cross-section for taking measurements is horizontal.

BRIEF DESCRIPTION OF THE DRAWINGS

The present disclosure is described in conjunction with the appended figures:

FIG. 1B is a schematic diagram of a multiphase flow meter with an extended venturi throat section and second microwave receiver-detector pair configured in accordance with an embodiment of the present invention;

Figure 1A:
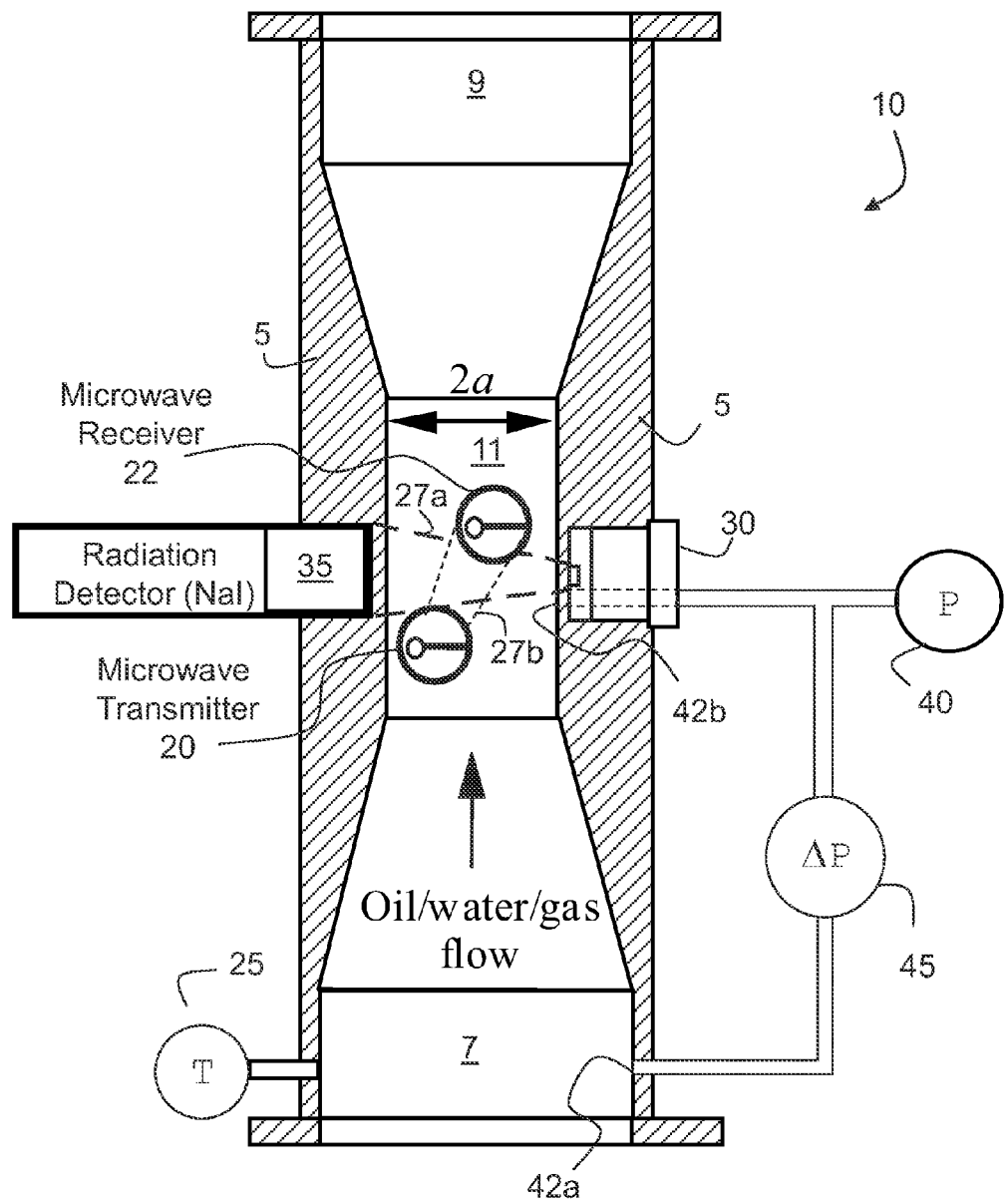
FIG. 1A is a schematic diagram of a multiphase flow meter configured in accordance with an embodiment of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiment(s) only, and is not intended to limit the scope, applicability or configuration of the invention. Rather, the ensuing description of the preferred exemplary embodiment(s) will provide those skilled in the alt with an enabling description for implementing a preferred exemplary embodiment of the invention. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

FIG. 1A is a schematic diagram of a multiphase flow meter configured in accordance with an embodiment of the present invention. In an embodiment of the present invention, a multiphase flow meter 10 may comprise a venturi 5 through which a multiphase fluid may flow and be measured. The venturi 5 may comprise an inlet 7, an outlet 9 and a throat section 11. In certain embodiments, the multiphase flow meter 10 may comprise the venturi 5 configured with a microwave transmitter 20 and a microwave receiver 22, a radiation source 30, a radiation detector 35, an absolute pressure sensor 40 and a differential pressure sensor 45. The differential pressure sensor 45 may comprise a first pressure port 42a located at the inlet 7 and a second pressure port 42b located at the throat section 11. In certain aspects, the absolute pressure sensor 40 and the differential pressure sensor 45 may be replaced by a processor (not shown) configured to process the absolute and differential pressures from pressure ports in the venturi 5. A temperature sensor 25 may also be used in the multiphase flow meter 10.

In an embodiment of the present invention, the microwave transmitter 20, the microwave receiver 22, the radiation source 30 and the radiation detector 35 may be installed the same cross-section of the throat section 11. In the illustrated embodiment, the microwave transmitter 20, the microwave receiver 22 are shown above and below the line 27a connecting the microwave transmitter 20 and the microwave receiver 22 for illustration purposes (line 27a is also referred to herein as plane A and/or the cross section). In the embodiment in which the microwave transmitter 20, the microwave receiver 22, the radiation source 30 and the radiation detector 35 are configured in the same cross-section, a transmission path 27b between the microwave transmitter 20 and the microwave receiver 22 may be coplanar. Further, the differential pressure sensor 45 may be configured with the pressure port 42b in the throat section 11 at the same cross-section as the microwave transmitter 20, the microwave receiver 22, radiation source 30 and radiation detector 35. Positioning of sensors in the same cross-section may provide for robust phase fraction measurements that do not require a further fluid-mechanics model interpretation for axially developing flow of the multiphase fluid.

In certain aspects, the venturi 5 is configured vertically providing that the multiphase fluid 2 may flow vertically upward through the venturi 5. In such aspects, stratified-like flow regimes may be eliminated and the phase distribution averaged over a relatively long duration may be treated as quasi-axisymmetric, which may provide for a reduction in the number of sensors necessary for measuring flow fractions and rates, etc. With the venturi in the vertical orientation, the measuring apparatus—i.e., the microwave transmitter 20, the microwave receiver 22, the radiation source 30, the radiation detector 35 and the pressure port 42b—may be configured on the same cross-section. Merely by way of example, the configuration of the measuring apparatus on the same horizontal cross-section of a vertical venturi may provide for reduced transmission paths of radiation and microwaves through the multiphase mixture and/or coincident mixture flow measurements.

The microwave transmitter 20 and the microwave receiver 22 may comprise at least one pair of microwave transmission and reception antennas (Tx-Rx) and the pair of antennas may be flushed mounted in the venturi 5—so that they do not intrude into the venturi 5—and may be positioned opposite one another in the venturi. The antennas may be cavity-backed type antennas with a square or circular aperture, and may comprise at least a single-dipole. U.S. Pat. No. 5,243,290 discloses various types of antennas technology and is incorporated by reference herein in its entirety for all purposes.

The microwave transmitter 20 and the microwave receiver 22 may comprise a single current-probe configured circumferential to the pipeline with an equivalent magnetic dipole parallel to the pipeline axis so that it may excite TE modes in the pipe, which, consequently, may act as a waveguide. The cavity of the antenna may be sealed by using a suitable dielectric material—such as a stable high-pressure-high-temperature ceramic. In certain embodiments of the present invention, the microwave transmitter 20 and the microwave receiver 22 may operate at microwave frequencies between 300 MHz and 1 GHz. In certain aspects the microwave transmitter 20 and the microwave receiver 22 may be configured to operate at dual frequencies, including but not limited to frequencies of 400 and 800 MHz.

In some embodiments of the present invention, the radiation source 30 may be a single high-energy source—such as $^{137}$Cs configured with a metal window—or a dual-energy source with a low-energy transparent window. In certain aspects, a water-cut measurement may be provided from a dual-energy source alone in combination with a radiation detector—which is sensitive to changes in fluid composition (reflected in the low-energy mass attenuation), but is insensitive to fluid distribution since both energy beams traverse the same path across the fluid mixture. The high-energy source may provide for obtaining a mixture density measurement and may be almost insensitive to fluid composition, but may tend to provide less accuracy under fresh-water/dense-oil situations due to the small density contrast between the water and oil.

By integrating the microwave transmitter 20, the microwave receiver 22, the radiation source 30 and radiation detector 35 at the same vertical pipe cross-section in the venturi 5, the effect of axial phase-fraction variation along the venturi 5 may be minimized and the radial phase distribution—largely axi-symmetric with time averaging—may be modeled. Further, by integrating the microwave transmitter 20, the microwave receiver 22, the radiation source 30 and radiation detector 35 at the same vertical pipe cross-section in the venturi 5, further interpretation of measurements is not necessary and inaccuracies may avoided since microwave transmission and radiation transmission through the multiphase fluid are measured coincidentally through the same cross-section of the multiphase fluid. In certain embodiments, microwave transmission through the venturi 5 may be used to track water salinity from the relation between the measured permittivity and conductivity of the multiphase fluid 2. In such embodiments, a more robust water-cut measurement may be possible since water-cut measurements may be produced that compensate for the salinity changes.

From the microwave transmission data, water-continuous and oil-continuous flows may be readily detected from the measured mixture permittivity and conductivity—for oil-continuous flows both the permittivity and conductivity will be low values. The on-line detection of the continuous liquid phase and the measured water-cut may provide information needed for accurate determinations of liquid viscosity—based on Einstein's law—the gas-liquid velocity slip and the venturi discharge coefficient.

High activity radiation sources and related detectors may be used to determine mixture density on a fast basis. In contrast, low activity radiation sources and related detectors may only be able to determine an average density from averaging of radiation measurements over a long period of time—of the order of multiple seconds or minutes. As a result, density measurements for low activity source systems may under-estimate mixture density when mixture density changes and is not constant for long periods. Such under estimates may significantly reduce the accuracy and effectiveness of a MPFM incorporating a low activity source. In certain embodiments of the present invention, parameters that have a relationship to density—such as pressure differential, water holdup and/or the like—may be monitored on a fast basis—less than a second—and the fast changes of the related parameter may be used to reconstruct mixture density from the radiation readings on a fast basis.

In an embodiment of the present invention, the radiation source 30 may comprise a low activity high-energy radiation source—a gamma radiation source less than or equal to one millicurie. In certain aspects, the radiation source 30 may comprise an exempt source as defined by the Nuclear Regulatory Commission ("NRC") in accordance with 10 C.F.R. section 39.35, which provides that sealed sources that are beta- or gamma-emitting radioactive material with an activity of 3.7 megabecquerels (100 microcuries) or less are exempt from leakage testing. Use of a low-activity source may reduce regulatory oversight, monitoring requirements and/or the like and may increase the safety of the MPFM. Further, use of exempt radiation sources in a sealed container/system removes the requirement of leakage testing, which may be extremely difficult and expensive in situations where the MPFM is installed in a hydrocarbon transporting pipeline associated with an oil rig or the like. However, low activity radiation sources, because of a low photon count-rate and the like, do not provide for fast/real-time density measurements or high accuracy.

In an embodiment of the present invention, the radiation source 30 may comprise a low-activity and/or exempt source and, merely by way of example, the differential pressure sensor 45 may provide for measurement of differential pressure in the venturi 5 as the multiphase fluid passes through the venturi 5. In different embodiments, other parameters with a density relationship may be measured—i.e., for single-phase gas and liquid density calculations at line conditions, pressure and temperature measurements of the fluid may be determined from the pressure sensor 40 and the temperature sensor 25.

Multiphase flows typically have fairly stable total mass flow rate (Q) over many minutes time-scale. The gas and liquid volume flow rates $q_G$ and $q_L$, respectively, may change due to mixture density change, according to the following:

$$Q = \rho_G q_G + \rho_L q_L$$

where $\rho_G$ and $\rho_L$ are gas and liquid densities.

In an embodiment, the differential pressure sensor 45 may provide for fast, for example on the order of fractions of seconds, venturi differential pressure measurement ($\Delta p(t)$) that may be used to track the changing mixture density ($\rho_m(t)$). The differential pressure is related to the mixture density according to equation (1).

$$\Delta p(t) = K_v Q^2 / \rho_m(t) \quad (1)$$

where $K_v$ is the venturi constant and is equal to $(1-\beta^4)/[2C_d^2 A_T^2]$, $\beta$ is equivalent to the venturi throat-to-inlet diameter, $C_d$ is equal to the venturi discharge coefficient and $A_T$ is equal to the venturi throat cross-sectional area.

The long-time, for example in the order of minutes, average version of equation (1) may be rewritten as equation (2).

$$<\Delta p> = K_v <Q>^2 / <\rho_m> \quad (2)$$

Taking the ratio of Equation (1) and (2) —noting that $<Q> = <Q(t)> \approx Q(t)$ provides the relationship shown in equation (3).

$$\rho_m(t) \approx <\rho_m> \Delta p(t) / <\Delta p> \quad (3)$$

For gas-liquid flows, for example, the above slow and fast gamma-ray mixture densities may be related to the count-rate $N_m$ as follows:

$$(\rho_m(t) - \rho_G)/(\rho_L - \rho_G) = \log[N_m(t)/N_G]/\log(N_L/N_G) \quad (4a)$$

$$(<\rho_m> - \rho_G)/(\rho_L - \rho_G) = \log[<N_m>/N_G]/\log(N_L/N_G) \quad (4b)$$

where $N_m$, $N_G$ and $N_L$ are the gamma-ray count-rates (counts per second) of the gas-liquid mixture, the gas and liquid, respectively. $<N_m>$ is the count measured by a low-activity or exempt source over a long period of time (minutes). From equations (4a) (4b) and (3), the fast gamma-ray count-rates—as would be measured by a high-activity source—may be estimated as $$\log[N_m(t)/N_G]/\log[<N_m>/N_G]$$

$$= [\rho_m(t) - \rho_G]/[<\rho_m> - \rho_G]$$

$$= [<\rho_m> \Delta p(t) / <\Delta p> - \rho_G]/[<\rho_m> - \rho_G] \quad (5)$$

Equation (5) above may provide for a re-estimate average mixture density for fast-changing flows—determined by fast differential pressure reading $\Delta p(t)$—by reducing the nonlinear logarithmic averaging errors that may occur in a determination from equation (4b) due to slow measurement (long averaging) of the low-activity or exempt-source measurement $<N_m>$.

With this understanding of the relationship between differential pressure change and density change, certain embodiments of the present invention may provide for determining the fast gamma-ray mixture density ($\rho_m(t)$) from long-average data—obtained from a low activity and/or exempt source—using the fast differential venturi pressure measurement measured by the differential pressure sensor 45, absolute pressure sensor 40, a combination of both and/or the like.

In another embodiment of the present invention, the fast gamma-ray mixture density ($\rho_m(t)$) may be derived from the long-average data—obtained from a low activity and/or exempt source—and a fast microwave water holdup ($\alpha_w(t)$) measurement determined from the microwave transmission. In certain aspects, water holdup ($\alpha_w(t)$) may be derived from fast mixture conductivity ($\sigma_m(t)$) and fast mixture permittivity ($\in_m(t)$) measurements, which in turn may be determined from fast microwave transmission magnitude and phase data. This alternative embodiment was developed to take advantage of the close synchronization between venturi pressure change ($\Delta p(t)$) and water holdup ($\alpha_w(t)$).

FIG. 1B is a schematic diagram of a multiphase flow meter with an extended venturi throat section and second microwave transmitter-receiver pair configured in accordance with an embodiment of the present invention. In one embodiment of the present invention, the venturi 5 may have a throat section 11 that is extended to provide for positioning a velocity-measuring antenna pair 50 in the throat section 11. The output from the velocity-measuring antenna pair 50 may be cross-correlated with the output from the microwave transmitter 20 and microwave receiver 22 to determine the velocity of the flow of the multiphase fluid.

When total mass flow rate through the venturi is low and the differential-pressure measurement is small, the cross-correlation technique can provide a complementary flow rate measurement. The two sets of antennas, the velocity-measuring antenna pair 50 and the microwave transmitter 20 and microwave receiver 22 may have a short axial spacing, i.e., of the order of about 100 mm for a 50 mm venturi-throat diameter between the antenna planes—plane A 27a and plane B 27b. This short spacing may provide for signal coherence and, as a consequence, a good cross-correlation flow velocity measurement (transit-time resolution 0.1 ms). For vertical three-phase flows, cross-correlation velocity closely follows the reference liquid velocity—calculated at plane A 27a from measured gamma-ray liquid holdup and reference liquid flow rate. About 10% positive bias is however noticeable, attributed to the liquid-holdup evolution along the venturi throat—decreasing from plane A 27a to plane 27b. Applying a 10% correction leads to a measure of liquid velocity at plane A 27a to within 10% of reading for gas-cuts (GVF) up to 95%. At GVF greater than 95% the reference liquid velocity shown may be unreliable due to the underestimate of liquid-holdup by the gamma-ray system. Microwave transmission cross-correlation measurement of velocity across the extended throat section may be capable of measuring the wet-gas liquid-film velocity. The microwave cross-correlation system may also have the potential of measuring water fraction in the (gas-water) wet-gas stream.

A single microwave Doppler probe (not shown) may be flushed mounted at the throat section 11 with a 45 degree emitting angle oblique with flow axis to provide alternative flow velocity measurement. This probe may provide for measurement of liquid velocity of 3-phase flows with an accuracy within 10% of actual flow velocities.

The velocity of wet-gas in the multiphase mixture may be made by using the Doppler shift of microwaves propagating in a circular pipe waveguide, formed by the venturi 5, when the wave is reflected of a moving volume-fraction (dielectric) discontinuity. An excitation antenna, not shown, may be used at an appropriate frequency, e.g. about 4 GHz in a 2 inch pipe, to launches only the TE11 propagating wave in a pipe, and two receiving antennas (not shown) located axially downstream may be used to detect Doppler shifted waves. The fast-moving cloud of liquid droplets—traveling at close to the carrying gas velocity—may form a spatial discontinuity in the dielectric constant, and, consequently, velocity of the wet-gas may be provided for using the Doppler shift system of antennas; wherein determination of the Doppler frequency may lead to the estimate of wet-gas velocity. The phase-difference of the two receivers can give estimate of flow mixture dielectric constant and thus the wave velocity needed in Doppler frequency calculation.

Figure 3:
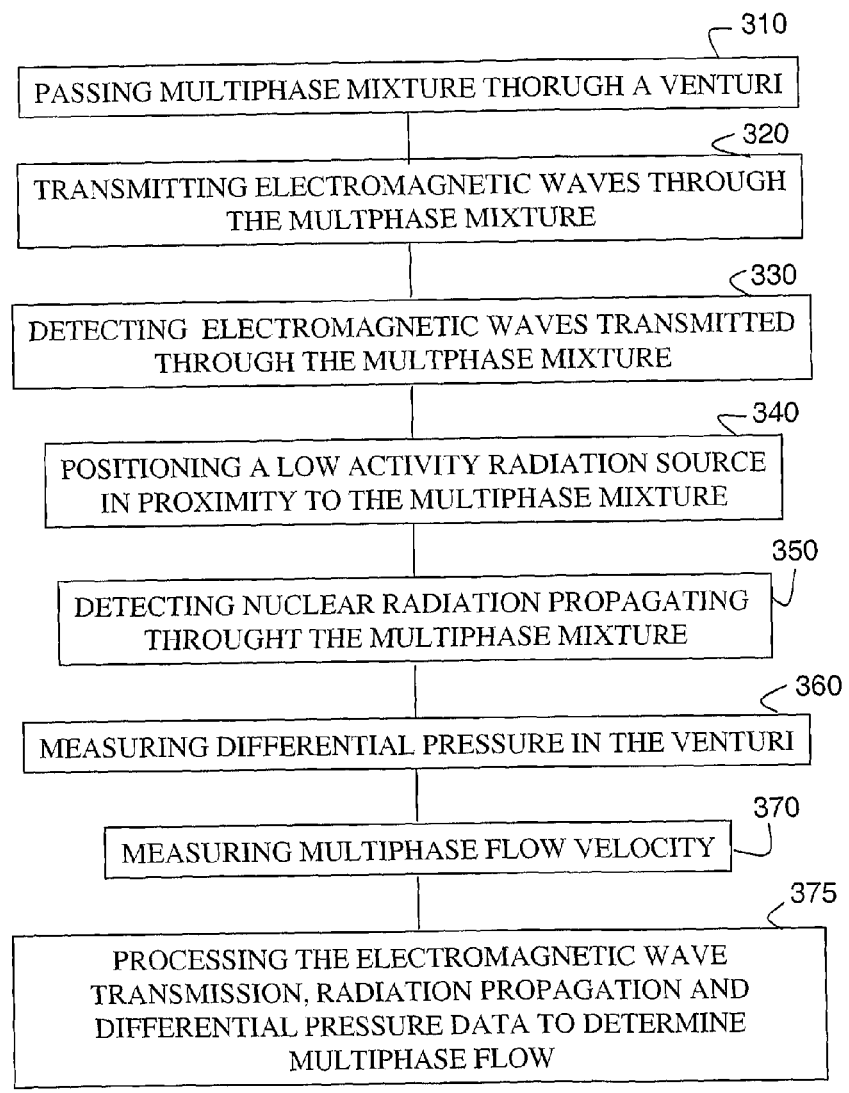
FIG. 3 is a flow chart type diagram illustrating operation of a multiphase flow meter in accordance with an embodiment of the present invention.

FIG. 3 is a schematic diagram of dual-frequency transmission microwave electronics for controlling a pair of antennas that are mounted opposite each other at the same cross-section as a gamma-ray source-detector pair in a multiphase flow meter in accordance with an embodiment of the present invention. For a desired intermediate-frequency (IF) that may be several tens of kilohertz, two frequency synthesizers, a first frequency synthesizer 210 and a second frequency synthesizer 220—which may be in certain aspects devices based on phase-locked loops connected to a reference clock 205—may generate two microwave frequencies, a first microwave frequency MWF1 and a second microwave frequency MWF2. In some embodiments of the present invention MWF1 may be equal to approximately 800 MHz and MWF2 may be equal to approximately 400 MHz. Two corresponding local oscillator frequencies LO1 and LO2 may also be generated by first local oscillating frequency synthesizer 230 and second local oscillating frequency synthesizer 240 respectively. The local oscillator frequencies my chosen to provide for the following: LO1=MWF1+IF and LO2=MWF2+IF. The output of the frequency synthesizers 210 and the frequency synthesizer 220 may be isolated by amplifiers 250 and 260 and isolators 255 and 265, respectively. A Tx Switch 270, that may be a transmit frequency switch, may select one of the microwave transmitting frequencies—MWF1 or MWF2—at the outputs of the isolators 255 and 265. A LO switch 262 may select a matching local oscillating frequency signal—either LO1 or LO2—and the selected local oscillating frequency may then be amplified by an LO amplifier 263.

For each selected microwave frequency, a directional coupler 272 may sample a small fraction of the transmitted power as the incident signal while the main fraction of the microwave frequency may be applied to a transmitting antenna Tx 275. The microwave signal transmitted through the multiphase flow mixture 2 in the pipe may detected by the receiving antenna Rx 277 and further amplified by a low-noise amplifier 280 to generate a transmitted signal 283.

In an embodiment of the present invention, the transmitting antenna Tx 275 and the receiving antenna Rx 277 are located opposite each other on either side of the throat section 11 of a venturi through which the multiphase fluid 2 is flowing. The radiation source 30 and the radiation detector 35 may also be configured opposite each other at the throat section 7 of the venturi. In certain aspects of the present invention the transmitting antenna Tx 275, the receiving antenna Rx 277, the radiation source 30 and the radiation detector 35 are configured in the same cross-section of the throat section 7 of the venturi.

A receive switch 285 may select alternately the incident signal 279 and the transmitted signal 283 for down-conversion to the respective IF signal 293 by a mixer 290 that may then be passed through a low-pass filter 291 amplified by an amplifier 294 that may be connected to an IF filter (not shown). Voltage waveforms of the incident signal 279 and the transmitted signal 283 may be digitized by an analog to digital converter 295.

The amplitude and phase of the incident signal 279 and the transmitted signal 283 may be reconstructed by a digital signal processing unit 299 that may also control the sequencing of all the switches, including Tx switch 270, Rx switch 285 and LO switch 261. The digital signal processing unit 299 may also set gain and/or attenuation of the amplifiers 250 and 260. The absolute amplitude-attenuation and phase-shift of the transmitted signal 283 may be calculated from amplitude ratio and phase difference of the transmitted signal 283 with respect to the incident signal 279. Amplitude scaling and phase-offset calibration factors may be determined with a network analyzer or the like based upon comparing microwave frequencies measurements for an empty pipe.

Processing of amplitude ratio and phase difference of the transmitted signal may provide for estimating mixture permittivity and conductivity of the multiphase fluid 2. Combining the mixture permittivity and conductivity of the multiphase fluid 2 with the mixture density of the multiphase fluid 2, which may be derived from the output of the radiation detector 35, water holdup and water-cut may be estimated. These computations may be performed by the digital signal processor 299 with the numerical results converted to a form suitable for transmission via a communication interface 298 and display (not shown).

Figure 2:
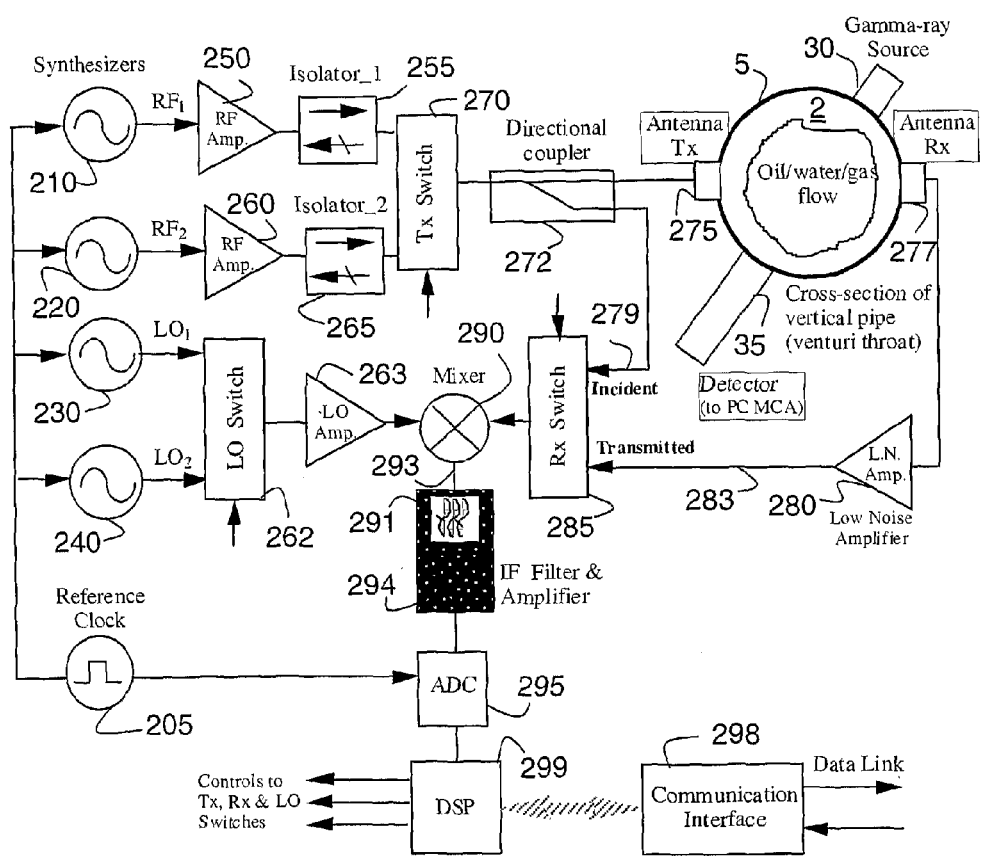
FIG. 2 is a schematic diagram of dual-frequency transmission microwave electronics for controlling a pair of antennas that are mounted opposite each other and at the same cross-section as a gamma-ray source-detector pair in a multiphase flow meter in accordance with an embodiment of the present invention.

In embodiments of the present invention, the amplitude and phase measured by the microwave electronics, such as the configuration described in FIG. 2 or the like, may be converted into the fundamental parameters governing the electrical properties of the multiphase fluid—i.e. the mixture permittivity and mixture conductivity. The water fraction ($\alpha_w$) of the multiphase fluid of for example well-mixed water/oil flow mixtures may then be determined by the appropriate use of permittivity and conductivity mixing laws. Equations 6, 7 and 8 below, illustrate simplified Ramu-Rao and Bruggeman mixing laws that may be used for this purpose. To use the mixing law analysis, knowledge of the liquid-phase continuous state of the multiphase liquid may be necessary. This understanding of the liquid-phase continuous state of the multiphase liquid may be obtained from a comparison of measured phase-shift, transformed mixture permittivity and/or conductivity with threshold values—where the threshold values may be determined for multiphase fluid mixtures theoretically, experimentally and/or the like.

Equations 6, 7 and 8 below show the relationship of homogeneous oil-water mixture permittivity $\varepsilon_m$ and conductivity $\sigma_m$ based on simplified Ramu-Rao and Bruggeman mixing formulae.

Using the Ramu-Rao mixing formula for water continuous flows, mixture permittivity and conductivity may be described according to the following equations:

$$\varepsilon_m = \varepsilon_w \frac{2\alpha_w}{3 - \alpha_w} \quad (6)$$

$$\sigma_m = \sigma_w \frac{2\alpha_w}{3 - \alpha_w} \quad (7)$$

where $\varepsilon_w$ and $\sigma_w$ are water permittivity and water conductivity, respectively.

Using the Bruggeman mixing formula for oil continuous flows, permittivity may be described according to the following equation (conductivity is largely not relevant for the oil continuous flow because of the lack of conductivity of hydrocarbons):

$$\varepsilon_m = \frac{\varepsilon_{oil}}{(1-\alpha_w)^3} \qquad (8)$$

For a lossy dielectric mixture, the complex wave propagation constant $\gamma_m$ may be expressed as:

$$\gamma_m = \alpha_m + j\beta_m \qquad (9)$$

with $\alpha_m$ being the attenuation constant (in units of neper/m) and $\beta_m$ the phase constant (radian/m).

Denoting L as the effective path-length from the transmission antenna Tx 275 and the reception antenna Rx 277, the transmission amplitude-attenuation M (dB) and phase-shift θ(radian) may be related to $\alpha_m$ and $\beta_m$ as:

$$\alpha_m = (M-M_o)/(8.686L) = \Delta M/(8.686L) \qquad (10)$$

$$\beta_m = (\theta-\theta_o)/L = \Delta\theta/L \qquad (11)$$

where $M_o$ and $\theta_o$ are respectively the amplitude and phase offsets of the transmission antenna Tx 275 and the reception antenna Rx 277 pair. Merely by way of example, in embodiments of the present invention in which cavity-backed antennas with square-apertures of dimension 18×18 mm or circular-apertures with diameter equal to 15 mm are installed in the throat section with and the throat section has a radius of 26 mm, the unified transmission model parameters have been found as:
$M_o = 29.2 + M_{oil}$ (dB), $\theta_o = \theta_{oil}$ with L=50 mm.

In a metallic pipe of inner radius α:

$$\gamma_m^2 = k_c^2 - k_m^2 \qquad (12)$$

where $k_c$ is the cutoff wave number of the $TE_{11}$ dominant mode ($k_c = 1.84/\alpha$),
$k_m$ is the wave number of the mixture of complex permittivity $\in_m^* = \in_m - j\sigma_m/(\in_o \omega)$.

At angular frequency ω, $$k_m^2 = \omega^2 \mu \in_o \in_m^* \qquad (13)$$

Equating real and imaginary parts of $\gamma_m^2 = k_c^2 - k_m^2$ leads to the mixture permittivity $\in_m$ and conductivity $\sigma_m$:

$$\in_m = (c_o/\omega)^2(k_c^2 - \alpha_m^2 + \beta_m^2) \qquad (14)$$

$$\sigma_m = 2\alpha_m \beta_m/(\omega\mu) \qquad (15)$$

Utilizing the above equations, the permittivity and conductivity of the multiphase fluid may be determined from the attenuation and/or the phase shift of the microwave signal transmitted through the multiphase fluid at the throat of the venturi. It may be observed that, for water-continuous and oil/water flows, a good agreement with the respective Ramu-Rao predictions is achieved at all water conductivities and frequencies. For oil-continuous flows and oil/water flows, a good matching of permittivity ($\in_m$) with the Bruggeman estimate may be achieved at a higher frequency. Both permittivity ($\in_m$) and conductivity ($\sigma_m$) are low for oil continuous flows.

From the analysis of results obtained from the multiphase flow meter using only microwave transmission measuring techniques and applying the formulas above, it may be observed that water holdup tends to be underestimated as the water-in-liquid ratio ("WLR") approaches the phase-continuous transition, which may be due to the water-oil velocity slippage. To overcome this under-prediction, generally caused by the effects of gas on the non-uniform permittivity and conductivity distribution of the mixture and on their effective values, an embodiment of the present invention provides for a three-species annular flow model incorporating a gamma-ray mixture density ($\rho_m$) measurement. The model may provide for an annular liquid-rich layer near the wall of the pipe with a gas core present at the pipe centre and assuming gas permittivity is equal to 1.0 and gas conductivity is equal to 0. Inside the liquid-rich layer, it is assumed that the water and oil are well mixed with negligible entrained gas and the water-holdup—with respect to the area of the liquid-layer—is denoted as $\alpha_{w,LF}$.

The annular 3-species mixing model is summarized in equations 19a, 19b, 20a and 20b below. Equation 19a relates the permittivity of the overall mixture to the permittivity of the well-mixed liquid-layer and the central gas-core, with weighting factors being their respective area fractions. Equation 19b is the counterpart relating conductivity. Examples of the 3-species mixing models are listed for water-continuous and oil-continuous flows based on the simplified Ramu-Rao and Bruggeman mixing laws, respectively.

The water-holdup $\alpha_w$ and in-turn the water-cut ($\alpha_{w,LF}$) may be derived from the three-species model described in the four equations (19a, 19b, 20a and 20b) based upon the permittivity and/or conductivity of the multiphase fluid determined from microwave transmission readings and the mixture density—determined from radiation transmission—where single-phase densities and electrical properties (permittivity and/or conductivity) are treated as known. The mixture density determined from a high-energy gamma-ray radiation source or the like may be calibration free. Water conductivity and permittivity may be tracked on-line in a robust manner with a microwave open-coaxial reflection probe flushed mounted at the liquid-rich region at the pipe wall. Water density may be estimated from its conductivity when the dominant salt species, for example sodium chloride, is known.

When water is continuous, in certain aspects of the present invention, conductivity may be used instead of permittivity in the 3-species mixing model because, due to the fluctuating nature of gas-liquid flows, there may be time-averaging errors both in the amplitude-phase to permittivity-conductivity conversion process, and in the permittivity-conductivity to water-holdup conversion process and the time-averaging error in the mixture permittivity—and the subsequent water holdup prediction—is apparently larger. However, in contrast, the amplitude-phase to conductivity transformation is found to be linear.

Equations 19a, 19b, 20a and 20b below show three-species gas-liquid two-layer mixing models based on a simplified Ramu-Rao and Bruggeman mixing formulae (for a well-mixed liquid layer where x and y are empirical exponents and all single-phase permittivity ($\in_g$, $\in_{oil}$ and $\in_w$), conductivity $\sigma_w$ and densities ($\rho_g$, $\rho_o$, and $\rho_w$) are assumed known). Equations 16a, 16b, 17 and 18 show the relationships for permittivity, conductivity, mixture density and water hold up for the mixture.

$$\text{Mixture permittivity: } \in_m^x = \alpha_{LF}\in_{LF}^x + (1-\alpha_{LF})\in_g^x \qquad (16a)$$

$$\text{Mixture conductivity: } \sigma_m^y = \alpha_{LF}\sigma_{LF}^y + (1-\alpha_{LF})\sigma_g^y$$
$$\sigma_g^y = \alpha_{LF}\sigma_{LF}^y \qquad (16b)$$

$$\text{Mixture density: } \rho_m = (1-\alpha_{LF})\rho_g + \alpha_{LF}[(1-\alpha_{w,LF})\rho_o + \alpha_{w,LF}\rho_w] \qquad (17)$$

$$\text{Water-holdup: } \alpha_w = \alpha_{w,LF}\alpha_{LF} \qquad (18)$$

The mixed oil/water liquid flow (no gas) is a special case of the two-layer gas-liquid model (with $\alpha_{LF} \to 1$). Equation 17 May be Solved by Iteration for the Example Cases Below. Using Ramu-Rao mixing laws for water continuous mixtures the water holdup and water cut may be shown with regard to mixture conductivity as having the following relationships:

$$\alpha_{w,LF} = 3\sigma_{LF}/(\sigma_{LF} + 2\sigma_w) \quad (19a)$$

$$\alpha_{LF} = (\sigma_m/\sigma_{LF})^y \quad (19b)$$

Substituting $\alpha_{LF}$ and $\alpha_{w,LF}$ into equation 17 may solve for $\sigma_{LF}$ (and then for $\alpha_{LF}$, $\alpha_{w,LF}$ and $\alpha_w$).

Using Bruggeman mixing laws for oil continuous mixtures the water holdup and water cut may be shown with regard to mixture permittivity as having the following relationships:

$$\alpha_{w,LF} = 1 - (\epsilon_{oil}/\epsilon_{LF})^{1/3} \quad (20a)$$

$$\alpha_{LF} = (\epsilon_m^x - \epsilon_g^x)/(\epsilon_{LF}^x - \epsilon_g^x) \quad (20b)$$

Substitute $\alpha_{LF}$ and $\alpha_{w,LF}$ into equation 17 may solve for $\epsilon_{LF}$ and then for $\alpha_{LF}$, $\alpha_{w,LF}$ and $\alpha_w$.

The accuracy of WLR measurement in some embodiments of the present invention that use radiation transmission measurements may be dependent on the calibration of mass attenuations of brine water, oil and gas. The brine water mass attenuation at low-energy may depend on the water salinity and salt species of the brine water and, as such, departure from the calibration conditions will result in erroneous WLR predictions. Taking into account the fact that most formation waters are dominated by the NaCl salt species (typically 90% of the total dissolved solids), it may be feasible to utilize microwave on-line water conductivity measurements to achieve correction to the brine low-energy mass attenuation. From relatively fresh-water to NaCl salt saturated water, the brine low-energy mass attenuation may be corrected to within about 2% by using brine salinity estimates determined from the conductivity of the mixture. Without the brine conductivity information, the relative error in the brine low-energy mass attenuation may be up to 50%. Since a 1% absolute change in brine salinity is largely detectable by using microwave conductivity, in the absence of single-phase density and gamma-ray statistical errors, the maximum (at WLR=1 and when gas-free) absolute error of the gas holdup is about 1%, that of the oil and water about 6% in absolute terms. The maximum WLR absolute error (at WLR=1) is also about 6%, independent of gas holdup.

In certain embodiments of the present invention, the flow velocity of the multiphase fluid may be determined from venturi differential pressure measurements. In other embodiments, particularly in embodiments using the full width or full-bore of the pipeline, flow velocity measurements may be determined based on the cross-correlation of dual-plane antenna signals. The second antenna pair is located at a cross-section further downstream or upstream from the location of the first pair. When combining the dual antenna pair with a venturi flow velocity measurement an extended-throat venturi can be used with the second pair of antennas installed for example at its downstream section as shown in FIG. 1B. When total mass flow rate through the venturi is low (thus the differential-pressure measurement is small), the cross-correlation technique may provide complementary flow rate measurement.

A single microwave Doppler probe may be flushed mounted at the venturi throat section with a 45 degree emitting angle oblique with flow axis to provide alternative flow velocity measurement. In certain aspects, such a velocity measurement may deliver liquid velocity of 3-phase flows with a high accuracy.

FIG. 3 is a flow chart type diagram illustrating operation of a multiphase flow meter in accordance with an embodiment of the present invention. In an initial step of an embodiment of the present invention, a multiphase fluid may be passed through a venturi. The venturi may comprise an inlet, a constriction and an outlet, where the constriction is elongated so as to have a continuous radius that is smaller than the radius of the pipeline through which flow is to be measured—the throat section—to which measuring apparatus—electromagnetic antennas, pressure sensors, radiation source and radiation detectors—may be coupled. In certain aspects, the venturi may be placed in line with a pipeline transporting hydrocarbons or may be attached to detour type pipes that may provide for sampling of the mixtures flowing through the pipeline.

In step 320, electromagnetic waves may be transmitted into the multiphase fluid as it passes through the throat section of the venturi from a transmitting antenna positioned in the throat of the venturi. In an embodiment of the present invention the electromagnetic waves are microwaves. In certain aspects, dual frequency microwaves of frequencies around 400 MHZ and 800 MHz may be transmitted into the multiphase fluid. In step 330, a receiving antenna may be used to receive the electromagnetic waves that have been transmitted through the multiphase fluid.

In step 340, a low activity radiation source is positioned in the throat of the venturi in proximity to the multiphase fluid. The radiation source may be a high-energy, low-activity source such as a low activity gamma ray source, an exempt gamma ray source, a sealed gamma ray source containing less than 100 µCi of a gamma emitting radionuclide and/or the like. In step 350 a radiation detector may be used to measure the radiation passing from the radiation source through the multiphase fluid. The radiation detector may be a semiconductor radiation detector or the like. In one embodiment of the present invention, the antennas for transmitting and receiving the electromagnetic waves and the radiation source and radiation detector may be configured in the same cross-section of the venturi.

In step 360, differential pressure of the multiphase fluid passing through the venturi may be measured. Merely by way of example, pressure ports may be positioned at the inlet and throat of the venturi to measure differential pressure and the differential pressure may be monitored on a fast basis—of the order of seconds, fractions of seconds or the like—as the multiphase fluid passes through the venturi. In step 370, velocity of the multiphase fluid may be determined from differential pressure readings in the venturi, from cross-correlation of outputs from antenna pairs and or the like.

In step 375, the electromagnetic wave transmission data, radiation transmission data and the differential pressure data may be processed to measure the multiphase fluid flow through the pipeline. Processing may be done by a computer, software application and/or the like. In an embodiment of the present invention, long-average mixture density, determined from radiation detection measurements, is interpreted into a fast mixture-density estimate using fast pressure differential measurements. This estimation of fast mixture-density measurement may provide for accurate fast mixture-density estimates using a low activity and/or exempt radiation source. The permittivity and/or conductivity of the multiphase fluid passing through the venturi may be processed from the phase change and/or amplitude attenuation of the electromagnetic waves passing through the venturi. Using the conductivity and or permittivity with the mixture density and the mixture velocity, as described in more detail above, a multiphase measurement of the mass flow rate or volume flow rate of the phases of the multiphase fluid may be determined.

While the principles of the disclosure have been described above in connection with specific apparatuses and methods, it is to be clearly understood that this description is made only by way of example and not as limitation on the scope of the invention.

The invention claimed is:

1. A method for measuring flow properties of phases in a multiphase mixture flowing in a conduit configured to transport liquid hydrocarbons at a location in the conduit, comprising:
flowing the multiphase mixture through a venturi, wherein the venturi comprises a constricting inlet, a throat section and a diverging outlet, and wherein a first internal diameter of the conduit is larger than a second internal diameter of the throat section, and measuring attenuation and phase shift of microwaves transmitted through the multiphase mixture in the throat section, wherein:
the microwaves are transmitted by a transmitting antenna and are received by a receiving antenna: and the transmitting antenna and the receiving antenna are coupled with the venturi; measuring a count rate of radiation detected by a radiation detector configured to detect radiation emitted from a radiation source, wherein:
the radiation detector and the radiation emitter are configured to provide that the radiation detector detects radiation emitted from the radiation emitter and that passes through the multiphase mixture in the throat section; and
the radiation source and the radiation detector are coupled with the venturi;
processing the count rate to determine a density of the multiphase mixture;
determining a mixture flow rate for the multiphase mixture; and processing the attenuation, phase shift, the density and the mixture flow rate to determine the flow properties of the multiphase mixture.

2. The method as recited in claim 1 wherein the transmitting antenna, receiving antenna, radiation source and radiation detector are configured on a cross-section of the throat section of the venturi.

3. The method as recited in claim 1 wherein the flow properties comprise at least one of water cross-sectional fraction, oil cross-sectional fraction, gas cross-sectional fraction, water volume flow rate, oil volume flow rate and gas volume flow rate.

4. The method as recited in claim 1 wherein the venturi is vertical and the cross-section is horizontal.

5. The method as recited in claim 1 further comprising:
measuring differential pressure in the venturi, wherein the differential pressure is measured between the constricting inlet and the cross-section.

6. The method recited in claim 1 wherein:
the attenuation and the phase shift are used to calculate at least one of permittivity of the multiphase mixture and conductivity of the multiphase mixture; and
the flow properties are determined from the mixture density and the at least one of the permittivity and the conductivity.

7. The method recited in claim 1 wherein the radiation source comprises a low activity source configured to emit high-energy radiation.

8. The method recited in claim 1 wherein the radiation source comprises a source of high-energy radiation with an activity of less than 100 microcuries.

9. The method recited in claim 7 further comprising:
measuring the count rate over a period of one or more minutes;
averaging the count rate measured over the period to determine an average count rate;
measuring differential pressure in the venturi, wherein:
the differential pressure is measured between the constricting inlet and the cross section; and the processing the count rate to determine the density of the multiphase mixture comprises processing the average count rate and the differential pressure.

10. The method recited in claim 7 further comprising:
measuring the count rate over a period of one or more minutes;
averaging the count rate measured over the period to determine an average count rate;
measuring the water holdup in the throat section of the venturi, wherein:
the water holdup is determined from the phase shift and the attenuation; and
the processing the count rate to determine the density of the multiphase mixture comprises processing the average count rate and the water holdup.

11. A method for measuring flow properties of phases in a multiphase mixture flowing in a conduit configured to transport liquid hydrocarbons at a location in the conduit, comprising:
flowing the multiphase mixture through a venturi, wherein the venturi comprises a constricting inlet, a throat section and a diverging outlet, and wherein a first internal diameter of the conduit is larger than a second internal diameter of the throat section;
measuring attenuation and phase shift of microwaves transmitted through the multiphase mixture in the throat section, wherein the microwaves are transmitted by a transmitting antenna and are received by a receiving antenna;
measuring a count rate of radiation detected by a radiation detector configured to detect radiation emitted from a radiation source, wherein the radiation detector and the radiation emitter are configured to provide that the radiation detector detects radiation emitted from the radiation emitter and that passes through the multiphase mixture in the throat section;
configuring the transmitting antenna, the receiving antenna, the radiation source and the radiation detector on a cross-section of the throat section of the venturi;
processing the count rate to determine a density of the multiphase mixture;
determining a mixture flow rate for the multiphase mixture; and
processing the attenuation, phase shift, the density and the mixture flow rate to determine the flow properties of the multiphase mixture.

12. The method as recited in claim 11 wherein the transmitting antenna, the receiving antenna, the radiation source and the radiation detector are each coupled with the venturi.

13. The method as recited in claim 11 wherein the flow properties comprise at least one of water cross-sectional fraction, oil cross-sectional fraction, gas cross-sectional fraction, water volume flow rate, oil volume flow rate and gas volume flow rate.

14. The method as recited in claim 11 wherein the venturi is vertical and the cross-section is horizontal.

15. The method as recited in claim 11 further comprising:
measuring differential pressure in the venturi, wherein the differential pressure is measured between the constricting inlet and the cross-section.

16. The method recited in claim 11 wherein:
the attenuation and the phase shift are used to calculate at least one of permittivity of the multiphase mixture and conductivity of the multiphase mixture; and
the flow properties are determined from the mixture density and the at least one of the permittivity and the conductivity.

17. The method recited in claim 11 wherein the radiation source comprises a low activity source configured to emit high-energy radiation.

18. The method recited in claim 17 wherein the radiation source comprises a source of high-energy radiation with an activity of less than 100 microcuries.

19. The method recited in claim 17 further comprising:
measuring the count rate over a period of one or more minutes;
averaging the count rate measured over the period to determine an average count rate;
measuring differential pressure in the venturi, wherein:
the differential pressure is measured between the constricting inlet and the cross-section; and
the processing the count rate to determine the density of the multiphase mixture comprises processing the average count rate and the differential pressure.

20. The method recited in claim 17 further comprising:
measuring the count rate over a period of one or more minutes;
averaging the count rate measured over the period to determine an average count rate;
measuring the water holdup in the throat section of the venturi, wherein:
the water holdup is determined from the phase shift and the attenuation; and
the processing the count rate to determine the density of the multiphase mixture comprises processing the average count rate and the water holdup.

21. A method for measuring flow properties of phases in a multiphase mixture flowing in a conduit configured to transport liquid hydrocarbons at a location in the conduit, comprising:
passing the multiphase mixture through a venturi, wherein the venturi comprises a constricting inlet, a throat section and a diverging outlet, and wherein a first internal diameter of the conduit is larger than a second internal diameter of the throat section;
determining at least one of permittivity of the multiphase mixture and conductivity of the multiphase mixture;
using a low activity radiation source to determine an average density of the multiphase mixture;
measuring a changing parameter, wherein the changing parameter changes in relation to changes in density of the multiphase mixture;
processing the average density and the changing parameter to determine a calculated density for the multiphase mixture;
determining a velocity of the multiphase mixture;
processing the velocity, the calculated density and at least one of the permittivity and the conductivity to determine the flow properties of the phases in the multiphase mixture.

22. The method as recited in claim 21 wherein the flow properties comprise at least one of water cross-sectional fraction, oil cross-sectional fraction, gas cross-sectional fraction, water volume flow rate, oil volume flow rate and gas volume flow rate.

23. The method as recited in claim 21 wherein the low activity radiation source comprises a high-energy radioactive material with an activity of less than 100 microcuries.

24. The method as recited in claim 21 wherein the permittivity is determined from amplitude attenuation and phase shift of microwaves transmitted through the multiphase mixture in the throat section of the venturi.

25. The method as recited in claim 21 wherein the conductivity is determined from amplitude attenuation and phase shift of microwaves transmitted through the multiphase mixture in the throat section of the venturi.

26. The method as recited in claim 21 wherein:
the velocity is determined from differential pressure of the multiphase mixture; and
the differential pressure comprises a difference in pressure between a first pressure of the multiphase mixture at the constricting inlet and a second pressure of the multiphase mixture at the throat section.

27. The method as recited in claim 21 wherein the velocity is determined from Doppler shift of electromagnetic waves transmitted through the multiphase mixture in the venturi.

28. The method as recited in claim 21 wherein the average density is determined from an average count rate of high-energy radiation emitted from the low activity radiation source and passing through the multiphase mixture in the throat over a period of one or more minutes.

29. The method as recited in claim 21 wherein:
the changing parameter comprises differential pressure; and
the differential pressure comprises a pressure difference between a first pressure of the multiphase mixture at the constricting inlet and a second pressure of the multiphase mixture at the throat section.

30. The method as recited in claim 21 wherein:
the changing parameter comprises water holdup; and
the water hold up is determined by measuring phase shift and attenuation of microwaves transmitted through the multiphase mixture in the throat section.

31. A system for measuring flow properties of a multiphase mixture flowing in a pipeline configured to transport liquid hydrocarbons at a location in the pipeline, comprising:
a measuring conduit for flowing the multiphase mixture through and configured to constrict the flow of the multiphase mixture, wherein the measuring conduit comprises an inlet, a constriction, a throat, an enlargement and an outlet, and wherein a first internal diameter of the inlet throat is larger than a second internal diameter of the throat;
means for transmitting microwaves through the multiphase mixture flowing through the throat;
means for receiving the microwaves transmitted through the multiphase mixture flowing through the throat;
means for measuring attenuation and phase shift of the microwaves transmitted through the multiphase mixture flowing through the throat;
means for calculating permittivity and conductivity of the multiphase mixture from the attenuation and the phase shift;
means for emitting high energy radiation into the multiphase mixture flowing through the throat;
means for detecting and counting the high-energy radiation emitted from the means for emitting and passing through the multiphase mixture flowing through the throat, wherein the means for transmitting microwaves, the means for receiving microwaves, the means for emitting high energy radiation and the means for counting high energy radiation are configured on a cross-section of the throat;

means for processing the radiation count to determine density of the multiphase mixture;

means for measuring differential pressure of the multiphase mixture between the inlet and the cross-section;

means for determining a flow rate of the multiphase mixture; and means for processing the conductivity, the permittivity, the density, the differential pressure and the flow rate to determine one of water cross-sectional fraction, oil cross-sectional fraction, gas cross-sectional fraction, water volume flow rate, oil volume flow rate and gas volume flow rate.

32. The system as recited in claim 31 wherein the means for emitting high energy radiation comprises a high-energy radioactive material with a low activity.

33. The system as recited in claim 32 wherein the means for emitting high energy radiation comprises a high-energy radioactive material with an activity of less than 100 microcuries.

34. The system as recited in claim 32 wherein:
an average count rate over a period of a minute or more is counted by the means for detecting and counting; and
the means for processing the radiation count to determine the density processes the density from the average count rate and the differential pressure.

35. A system for measuring flow properties of a multiphase mixture flowing through a pipeline configured to transport liquid hydrocarbons at a location in the pipeline, comprising:
a measuring conduit for flowing the multiphase fluid through and configured to constrict the flow of the multiphase fluid, wherein the measuring conduit comprises an inlet, a constriction, a throat, an enlargement and an outlet, and wherein a first internal diameter of the inlet throat is larger than a second internal diameter of the throat;
a first microwave antenna coupled with the measuring conduit and configured to transmit the microwaves through the throat;
a second microwave antenna coupled with the measuring conduit and configured to receive the microwaves transmitted through the throat;
a low-activity, high-energy radiation source coupled with the measuring conduit and configured to emit high-energy nuclear radiation into the throat;
a high-energy radiation detector coupled with the measuring conduit and configured to detect the high-energy radiation emitted from the radiation source and passing through the throat, wherein the first microwave antenna, the second microwave antenna, the radiation source and the high-energy radiation detector are configured on a cross-section in the throat;
an averaging processor capable of communicating with the high-energy radiation detector and configured to process an average count of the high-energy radiation detected by the high-energy radiation detector over a period of one or more minutes;
a differential pressure sensor coupled with the measuring conduit and comprising a first pressure port and a second pressure port, wherein:
the first pressure port is located at the inlet and the second pressure port is located at the cross-section; and
the differential pressure sensor is configured to monitor pressure differential between a first pressure of the multiphase fluid at the inlet and a second pressure of the multiphase fluid at the horizontal cross-section; and
a flow processor capable of communicating with the first and second microwave antennas, the averaging processor and the differential pressure sensor and configured to process microwave transmission data, average high-energy radiation transmission data and differential pressure data to determine the flow properties.

36. The system as recited in claim 35 wherein the flow properties comprise at least one of water cross-sectional fraction, oil cross-sectional fraction; gas cross-sectional fraction; and water volume flow rate, oil volume flow rate and gas volume flow rate.

37. The system as recited in claim 35 wherein the measuring conduit is vertical and the cross-section is horizontal.

38. The system as recited in claim 35, further comprising:
a transceiver coupled with the measuring conduit, wherein the transceiver comprises an electromagnetic wave transmitter and an electromagnetic wave receiver; and
a Doppler processor capable of communicating with the transceiver and configured to determine a flow rate of the multiphase mixture from a Doppler shift of a frequency of an electromagnetic wave transmitted between the electromagnetic wave transmitter and the electromagnetic wave receiver.

39. The system as recited in claim 35 wherein the radiation source for emitting high-energy nuclear radiation comprises a gamma-emitting radioactive material with an activity of less than 100 microcuries.

40. A pipeline section designed to carry flow from a hydrocarbon well, including at least one pair of microwave transmitter and receiver and at least one pair of radiation source and detector, wherein the pair of microwave transmitter and receiver and windows of the pair of radiation source and detector are located around essentially the same circumference perpendicular to the flow direction.

41. The pipeline section of claim 40, wherein the radiation source is an exempted source.

42. The pipeline section of claim 40, further including a flow velocity meter.

43. The pipeline section of claim 42 wherein the flow velocity meter is a venturi flowmeter and the circumference is located with the throat section of a venturi flowmeter.

44. The pipeline section of claim 42 wherein the flow velocity meter measures a Doppler shift.

45. The pipeline section of claim 42 wherein the flow velocity meter is designed to measure a correlation of one or more flow properties measured at the circumference and a second location along the flow direction.

* * * * *